(12) United States Patent
Hastedt et al.

(10) Patent No.: US 7,449,201 B2
(45) Date of Patent: *Nov. 11, 2008

(54) STORAGE STABLE POWER COMPOSITIONS OF INTERLEUKIN-4 RECEPTOR

(75) Inventors: Jayne E. Hastedt, San Carlos, CA (US); Kirsten M. Cabot, San Francisco, CA (US); David K. Gong, Foster City, CA (US); Dennis M. Hester, Richmond, CA (US)

(73) Assignee: Nektar Therapeutics, San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/644,150

(22) Filed: Dec. 21, 2006

(65) Prior Publication Data

US 2007/0122354 A1 May 31, 2007

Related U.S. Application Data

(63) Continuation of application No. 11/048,364, filed on Feb. 1, 2005, now Pat. No. 7,172,768, which is a continuation of application No. 10/032,238, filed on Dec. 21, 2001, now Pat. No. 6,896,906.

(60) Provisional application No. 60/256,786, filed on Dec. 21, 2000.

(51) Int. Cl.
*A61K 9/14* (2006.01)
*C07K 14/715* (2006.01)

(52) U.S. Cl. .................... 424/489; 424/46; 530/350
(58) Field of Classification Search .................. None
See application file for complete search history.

(56) References Cited

U.S. PATENT DOCUMENTS

| 5,599,905 A | 2/1997 | Mosley et al. |
|---|---|---|
| 5,767,067 A | 6/1998 | Arpaia et al. |
| 5,856,296 A | 1/1999 | Mosley et al. |
| 6,063,371 A | 5/2000 | Maliszewski et al. |
| 6,210,661 B1 | 4/2001 | Enssle et al. |
| 6,328,954 B1 | 12/2001 | Enssle et al. |
| 6,582,728 B1 | 6/2003 | Platz et al. |
| 7,172,768 B2 * | 2/2007 | Hastedt et al. .............. 424/489 |

FOREIGN PATENT DOCUMENTS

| WO | WO 90/05183 | 5/1990 |
|---|---|---|
| WO | WO 93/00951 | 1/1993 |
| WO | WO 94/21282 | 9/1994 |
| WO | WO 95/31479 | 11/1995 |
| WO | WO 96/09814 | 4/1996 |
| WO | WO 96/32149 | 10/1996 |
| WO | 01/08708 | 2/2001 |
| WO | 01/62272 | 8/2001 |

OTHER PUBLICATIONS

Borish et al., "Interleukin-4 Receptor in Moderate Atopic Asthma", Am. J. Respir. Crit. Care Med., 160(6):1816-1823.
Chen et al., "CD4+T Lymphocyte Modulation of Ozone-Induced Murine Pulmonary Inflammation", Am. J. Respir. Cell Mol. Biol., 12(4):396-403.
Cohn et al., "Th2-Induced Airway Mucus Production is Dependent on IL-4R alpha, But Not on Eosinophils", J. Immunol., 162(10):6178-6183.
Lange, "Interleukin 4 Receptor Immunex Corp.", Current Opinion in Cardiovascular, Pulmonary & Renal Investigational Drug 1999, 1(4):526-531, abstract.
Nossal, Nature, 162:36-37, (1948).
Sangwan et al., "Aerosolized Protein Delivery in Asthma; Gamma Camera Analysis of Regional Deposition and Perfusion", J. Aerosol Med., 14(2):185-195.

* cited by examiner

*Primary Examiner*—Prema Mertz
(74) *Attorney, Agent, or Firm*—Naishadh Desai; Mark A. Wilson

(57) ABSTRACT

The present invention provides storage stable dry powder compositions of IL-4R. The powder compositions demonstrate superior chemical and physical stability over their solution counterparts, particularly upon storage under varying conditions of temperature and humidity. Moreover, the powders, as prepared, possess good aerosol properties, which are maintained upon storage.

17 Claims, 2 Drawing Sheets

IL-4R Spray Dried Powders Temperature Effect on Monomer Content
(2 week Stability Data)

IL-4R Spray Dried Powders RH Effect on Monomer Content
(2 week Stability Data)

FIGURE 3

IL-4R Spray Dried Powder Compared to Solution Monomer Content
(2 week temperature stability data)

STORAGE STABLE POWER COMPOSITIONS OF INTERLEUKIN-4 RECEPTOR

CROSS-REFERENCE TO RELATED APPLICATIONS

This application is a continuation of U.S. patent application Ser. No. 11/048,364, filed Feb. 1, 2005, which is a continuation of U.S. patent application Ser. No. 10/032,238, now U.S. Pat. No. 6,896,906, issued May 24, 2005, which claims the benefit of priority of U.S. Provisional Patent Application Ser. No. 60/256,786, wherein the contents of each of the foregoing are incorporated herein by reference in their entireties.

FIELD OF THE INVENTION

The present invention generally relates to spray dried, inhaleable powder compositions of interleukin-4 receptor (IL-4R) and to methods for making and pulmonarily administering such compositions. The powders of the invention are particularly stable with respect to monomer content and aggregate level upon both preparation and storage, and additionally possess superior aerosol properties, even in the absence of stabilizing carriers or excipients. The powders of the invention, when administered to the deep lung, are useful for treating allergic diseases, such as asthma, atopy, and atopic dermatitis.

BACKGROUND OF THE INVENTION

Interleukin 4 (IL-4, also known as B cell stimulating factor, or BSF-1) is a cytokine produced by T helper cells, mast cells, and basophils. IL-4 has been shown to possess a broad spectrum of biological activities, including growth co-stimulation of T cells, mast cells, granulocytes, megakaryocytes, and erythrocytes. In addition, IL-4 stimulates the proliferation of several IL-2 and IL-3 dependent cell lines, induces the expression of class II major histocompatibility complex molecules on resting B cells, influences the production of IgE and enhances the secretion of IgE and IgG$_1$ isotypes by lipopolysaccharide-stimulated B cells. IL-4 has been identified to play a critical role in the development of allergic diseases, and is most commonly associated with asthma and allergies; or diseases characterized by difficulty breathing.

IL-4 binds to IL-4 receptor (IL-4R), an endogenous membrane-bound protein on the surface of certain cells. Upon such binding, IL-4R transduces a biological signal to various immune effector cells, thereby triggering a cascade of events that lead to clinical symptoms (Renz H et al., 1991, *J Immunol*, 146(9):3049-55). Nucleotide and protein sequence determination for IL-4R has been carried out. Mature human IL-4R has three domain structures: an extracellular domain (about 207 amino acids), a membrane passage region (about 24 amino acids), and an intracytoplasmic domain (about 569 amino acids) (European Patent No. EP 585-681 (1994)). Soluble IL-4R (sIL-4R) has also been isolated, cloned and extensively investigated (European Patent No. EP 367-566 (1997); Mosley et al., 1989, *Cell*, 59-335, 1989; U.S. Pat. No. 5,767,065 and Garrone P et al., 1991, *Eur J Immunol*, 21(6): 1365-9). IL-4 preferentially binds to sIL-4R in solution rather than to the endogenous cell-surface IL-4R, thereby preventing cellular activation and blocking the biological response, e.g., the cascade of effects associated with IL-4 and its binding to the endogenous receptor (Renz H et al., 1991, supra. and Renz, H, 1999, *Inflamm Res.*, 48(8): 425-31).

IL4-R has been described as an immunosuppressant and an anti-inflammatory agent, and administration of IL-4R may be beneficial in the treatment of conditions such as allergy, rhinitis, atopic dermatitis, rheumatoid arthritis, graft rejection, chronic graft-versus-host disease (GvH) and systemic lupus erthematosus (SLE) (See, e.g., U.S. Pat. No. 5,856,296; Renz H et al., 1992, *J Invest Dermatol*, 99(4):403-8; Hackstein H et al., 1999, *Tissue Antigens*, 54(5):471-7; Rivas D et al., 1995, *J Autoimmun*, 8(4):587-600; and Schorlemmer H U et al., 1995, *Inflamm Res*, 44 Suppl 2:S194-6).

Like many biopeptides, IL-4R tends toward instability. It tends to degrade and/or aggregate under extreme conditions (e.g., highly acidic or basic pH, high temperatures) and is susceptible to oxidizing agents and endogenous proteases. The inherent chemical and physical instability of IL-4R makes pharmaceutical formulation particularly problematic. To maintain the stability and bioactivity of the protein, current IL-4R formulations are primarily solution-based, and stored prior to administration as lyophilizates (e.g., U.S. Pat. Nos. 5,856,296; 5,767,065, and 6,063,371). A soluble, solution-based IL-4R peptide composition for administration by inhalation, Nuvance™, is currently in clinical trials for the treatment of asthma (Borish L C et al., 1999, *Am J Resp Crit Care Med*, 160(6): 1816-23).

Solution-based formulations of IL-4R suffer from drawbacks other than those associated with solution phase instability. First, solution-based formulations take up more room and require more care than solid formulations and, thus, are more costly. Moreover, in general, they must be refrigerated (typically maintained in an environment of 2 to 8° C.) which further restricts the storage and transport options. In addition, many solution-based formulations exhibit a protein concentration loss over time, which is presumably due to the formation of dimers and other protein aggregates in solution. Such formulations frequently must be supplemented with stabilizing additives such as buffers and/or antioxidants to minimize solution instability. Thus, it would be desirable to provide a solid or powder-based composition of IL-4R, particularly one that could not only be stably prepared and stored, but additionally administered in solid form, such as an inhaleable dry powder. Many preclinical and clinical studies with inhaled proteins, peptides, DNA and small molecules have demonstrated efficacy both within the lungs and systemically.

Powder formulations represent an alternative to solution formulations, and proteins, when desired in powder form, are most often prepared as lyophilizates (e.g., U.S. Pat. No. 5,856,296). Unfortunately, lyophilized powders are typically formed as cakes, which require additional grinding and milling, and optionally sieving processing steps to provide flowing powders. In the past few years, spray drying has been employed as an alternative approach for preparing a number of therapeutic protein-based powders, particularly for aerosolized administration (e.g., International Patent Publication Nos. WO 96/32149; WO 95/31479; WO 97/41833, assigned to Inhale Therapeutic Systems, Inc.). Unfortunately, certain proteins, and cytokines in particular, are prone to degradation during spray drying and loss of their secondary structure (Maa, Y. F., et al., *J. Pharm. Sciences*, 87 (2), 152-159 (1998)). For a representative cytokine, human growth hormone, Mumenthaler reported that spray drying at 90° C. resulted in 4% formation of insoluble aggregates and 21% formation of soluble aggregates—a loss of 25% intact protein (*Pharmaceutical Res.*, 11, 12-20 (1994)). The instability of the illustrative cytokine, hGH, was further demonstrated by Maa, Y. F., et al., ibid, who reported 42% aggregate formation (soluble and insoluble) upon atomization of a solution of hGH.

Additionally, sIL-4R possesses a number of potential instability sites leading to both solution and solid state-based instability. Specifically, sIL-4R contains 7 cysteines (Cys11, 21, 31, 51, 61, 63 and 184), ensuring at least one free sulfhydryl which may be available for intermolecular disulfide linkages. Such intermolecular disulfide linkages lead to the ready formation of dimers, trimers and other self-aggregates. Thus, this molecule is particularly prone to instability. In addition to sites susceptible to aggregation, the IL-4R peptide also has sites susceptible to degradation. For example, sites likely vulnerable to oxidative attack include four methionine residues (Met3, 16, 25, and 67). Additionally, an acid labile Asp-Pro linkage disruptable at low pH is found at amino acid residues 145-146. Two likely deamidation sites include Asn-Gly (26-27), and Asn-Gly (56-57), although the molecule possesses numerous other potential deamidation residues (Asn and Gln).

Thus, the challenge facing the inventors was not only to provide an improved dry powder formulation of IL-4R for overcoming some of the disadvantages associated with solution-based formulations of IL-4R as described above, but also to balance the factors affecting the instability and aerosol properties of IL-4R to arrive at a stable dry powder formulation suitable for pulmonary administration. That is to say, prior to the present invention, the development of a chemically and physically stable, bioactive dry powder of IL-4R that also possesses the physical properties necessary for aerosolization (e.g., high dispersibilities which remain stable over time, appropriate aerodynamic size) was unknown.

SUMMARY OF THE INVENTION

The present invention is based upon the unexpected discovery of chemically and physically stable spray dried powder compositions of IL-4R, even though such molecules (i.e., cytokines) are known to be particularly unstable when exposed to the shear stress, liquid-wall interactions, high temperature conditions and the like of spray drying. Surprisingly, the spray-dried powder of the invention exhibits both a monomer content and aggregate level that is essentially unchanged relative to that of its pre-spray dried solution. Moreover, the invention provides IL-4R dry powder compositions that are storage stable with respect to both monomer content and aggregate level, even under extreme conditions of humidity. That is to say, the spray dried powders described herein exhibit both superior chemical and physical stability, as well as having good dispersibilties, (i.e., aerosol properties) making them suitable for administration to the lung.

In one aspect, the invention provides a spray dried IL-4R powder composition that is capable of being stored for extended periods of time, 14 days or more, in extreme humitidy and temperature conditions without experiencing substantial alterations in aerosol performance, chemical and/or physical character, bioactivity, and the like. More particularly, the IL-4R content of the powder compositions of the present invention is essentially unchanged as compared to the pre-spray dried suspensions or solutions, i.e., experiencing minimal aggregate formation and/or protein monomer loss over time.

The IL-4R powder composition, demonstrating insignificant degradation upon preparation and storage, may be prepared in the absence of stabilizing additives or excipients, or may further include a pharmaceutically acceptable excipient. Preferred excipients include zinc salts, citrate, leucine, and combinations thereof.

The IL-4R powder composition preferably has a monomer content that is substantially unchanged as compared to that of the pre-dried solution or suspension. The change in monomer content is presented herein as a percent decrease (as compared to pre-dried solution or suspension). The decrease in monomer content is preferably less than about 10%, more preferably less than 7%, most preferably less than 5%.

The IL-4R powder composition preferably exhibits minimal aggregate formation as compared to that of the pre-dried solution or suspension. The level of aggregate formation is presented herein as a percent increase (as compared to pre-dried solution or suspension). The increase in aggregate content is preferably less than 10%, more preferably less than 7%, most preferably less than 5%.

Additionally, the IL-4R powder compositions of the invention comprise particles effective to penetrate into the alveoli of the lungs, that is, having in a particular embodiment, a mass median diameter (MMD) of less than about 10 μm, preferably less than about 7.5 μm, and most preferably less than 5 μm in diameter. In a particularly preferred embodiment, the powder is composed of particles having an MMD from about 1.0 to 3.5 μm.

Further embodiments of the IL-4R powder compositions in accordance with the invention include spray dried IL-4R particles having a mass median aerodynamic diameter (MMAD) of less than about 10 microns, preferably less than about 5.0 microns, and more preferably less than about 3.5 microns. In an especially preferred embodiment, the MMAD ranges from 1.5 to 3.5 microns.

Also encompassed by the invention is an aerosolized IL-4R powder formulation, and an IL-4R powder in a unit dosage form.

In another aspect, the invention is directed to a method for administering an IL-4R powder composition as described herein to the lungs of a patient in need thereof. In the method, a composition as described above is administered by inhalation in aerosolized form.

The invention also encompasses, in yet another aspect, a method for preparing a dispersible, dry IL-4R powder composition having the features described above.

In one embodiment, the respirable IL-4R powder composition is prepared by combining the active IL-4R agent(s) in a suitable solvent to form a mixture or solution and spray-drying the mixture or solution to obtain discrete, substantially amorphous particles, preferably in the form of a dry powder. The IL-4R remains essentially intact upon spray drying, resulting in powder particles in which the extent of protein degradation (as characterized by decrease in monomer content and aggregate formation) is insignificant.

An optional pharmaceutical excipient may be further added to the solvent to form a homogeneous solution or heterogeneous mixture, such that spray-drying of the solution or mixture produces particles comprising, in combination with IL-4R, excipient, buffer, and any other components which are present in the solution or mixture. Alternatively, the pharmaceutical excipient may be separately dissolved and spray dried to yield separate yet co-administrable powder particles.

These and other objects and features of the invention will become more fully apparent when the following detailed description is read in conjunction with the accompanying figures and examples.

BRIEF DESCRIPTION OF THE FIGURES

FIG. 1: This figure represents a graph of the effect of temperature on monomer content of spray dried powders, Formulations 1(A)-1(D) of Example 1 (2 week stability data).

FIG. 2: This figure represents a graph of the effect of relative humidity on monomer content of spray dried powder, Formulations 1(A)-1(D) of Example 1 (2 week temperature stability data).

FIG. 3: This figure represents a graph of the effect of temperature on monomer content of spray dried powders, formulations 1(A)-1(D) of Example 1 (2 week temperature stability data).

DETAILED DESCRIPTION OF THE INVENTION

A. Definitions

The following terms as used herein have the meanings indicated.

In the context of the present invention, "IL-4R" and "sIL-4R" refer to the extracellular domain of the cell-bound protein that acts as receptor for the cytokine, interleukin-4. As discussed below, IL-4R as used herein is not limited to a single peptide sequence, but is meant to encompass any known protein having IL-4R activity, including naturally and synthetically derived IL-4R as well as agonists and analogs thereof, to the extent that they retain the therapeutic activity associated with native peptide.

As used herein, the term "agonist" refers to compounds which mimic the effect of the native compound. An agonist may be a peptide or a non-peptide compound.

As used herein, the term "analog" refers to those compounds in which one or more amino acids have been substituted, deleted (i.e., fragments), added, or otherwise modified from the native (wild-type) human sequence, and which exhibits at least about 10, 20, 30, or 40%, and preferably at least 50%, 60%, or 70%, and most preferably at least 80%, 90%, 95%, 100% or greater than 100% bioactivity of that of the native (non-synthetic), endogenous peptide. The receptor specificity is optionally substantially similar to the native (wild-type), endogenous peptide. Typically, the receptor affinity will be at least 30%, 40%, or 50% that of the native (wild-type), endogenous peptide; more preferably at least 60%, 70%, 80%, 90%, 95%, 100% or greater than 100%.

Compositions of the present invention are considered to be "respirable" if they are suitable for inhalation therapy (i.e., capable of being inspired by the mouth or nose and drawn into the lungs) and/or pulmonary delivery (i.e., local delivery to the tissues of the deep lung and absorption through the epithelial cells therein into blood circulation). Compositions of the present invention are preferably suitable for rapid systemic absorption through the lungs, i.e., peaking in blood in less than 60 minutes.

As used herein, "deep lung" refers to the alveolar regions of the lung (as opposed to the bronchial regions). A composition suitable for "inhalation therapy", is one which, when aerosolized, may be (i) readily dispersed in an oral inhalation or intranasal delivery device, and (ii) inspired through either the mouth or nose by a mammalian subject so that at least a portion of the particles are absorbed through the mucous membranes of the nasal passages or the lung. A composition suitable for "pulmonary administration" comprises particles at least a portion of which, when delivered via inhalation in aerosolized form, reach the tissues of the lung, including the deep lung.

"Orally respirable" compositions are those respirable compositions that are particularly adapted for oral inhalation. Likewise, "nasally respirable" compositions are those respirable compositions that are particularly adapted for nasal inhalation, i.e., intranasal delivery into the upper respiratory tract.

"Dry powder" refers to respirable composition that contains finely dispersed solid particles that are relatively free flowing and capable of (i) being readily dispersed in an inhalation device and (iii) inhaled by a subject so that a portion of the particles reach the lungs to permit penetration to the alveoli. The dry powder may be crystalline, an amorphous glass or a mixture of both forms. A dry powder typically contains less than about 10% moisture, preferably less than about 5% moisture, and more preferably contains less than about 3% moisture.

"Emitted Dose" or "ED" provides an indication of the delivery of a drug formulation from a suitable inhaler device after a firing or dispersion event. More specifically, for dry powder formulations, the ED is a measure of the percentage of powder which is drawn out of a unit dose package and which exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-determined parameter, and is typically determined using an in-vitro device set up which mimics patient dosing. To determine an ED value, a nominal dose of dry powder, typically in unit dose form, is placed into a suitable dry powder inhaler (such as the described in U.S. Pat. No. 5,785,049, assigned to Inhale Therapeutic Systems) which is then actuated, dispersing the powder. The resulting aerosol cloud is then drawn by vacuum from the device, where it is captured on a tared filter attached to the device mouthpiece. The amount of powder that reaches the filter constitutes the emitted dose. For example, for a 5 mg, dry powder-containing dosage form placed into an inhalation device, if dispersion of the powder results in the recovery of 4 mg of powder on a tared filter as described above, then the emitted dose for the dry powder composition is: 4 mg (delivered dose)/5 mg (nominal dose)×100=80%. For non-homogenous powders, ED values provide an indication of the delivery of drug from an inhaler device after firing rather than of dry powder, and are based on amount of drug rather than on total powder weight. Similarly for MDI and nebulizer dosage forms, the ED corresponds to the percentage of drug which is drawn from a unit dosage form and which exits the mouthpiece of an inhaler device.

A "dispersible" powder is one having an ED value of at least about 30% preferably at least about 40%, more preferably at least about 50%, and even more preferably at least about 55%.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size (e.g., electron microscopy, light scattering, laser diffraction.

"Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, in air, as the particle. The aerodynamic diameter encompasses particle shape, density and physical size of a particle. As used herein, MMAD refers to the midpoint or median of the aerodynamic particle size distribution of an aerosolized powder determined by cascade impaction, unless otherwise indicated.

"Fine Particle Fraction" ($FPF_{<3.3 \mu m}$) is defined as the dose of powder which is under 3.3 microns as determined by cascade impaction. This parameter corresponds to the total mass under stage 3 of an Andersen impactor when operated at a flow rate of 1 cfm (28.3 L/min).

"Pharmaceutically acceptable excipient" and "pharmaceutically acceptable carrier" are synonymous and refer to excipients that may be included in the formulations of the invention and taken into the lungs in association with the particles with no significant adverse toxicological effects to the subject, and particularly to the lungs of the subject.

"Pharmacologically effective amount" or "physiologically effective amount" is the amount of IL-4R present in an inventive composition as described herein that is needed to provide a desired level of IL-4R in the bloodstream of tissue of a subject to be treated and thereby provide an anticipated physiological response when such composition is administered by inhalation for deposition in and absorption from the lung. The precise amount will depend upon numerous factors, e.g., the particular IL-4R used (e.g., natural or synthetic, full-length or fragment or analog), the delivery device employed, the physical characteristics of the powder, the intended patient use (e.g., the number of doses administered per day), and the patient considerations (e.g., age, size weight, health, etc.), and can be determined by one skilled in the art, based upon the information provided herein.

A "surface active agent" is an excipient having surface activity (measured, e.g., by surface tensiometry), as characterized by its ability to reduce the surface tension of the liquid in which it is dissolved and cause drugs associated with it to spread rapidly over mucosal surfaces. Surface tension, which is associated with the interface between a liquid and another phase, is that property of a liquid by virtue of which the surface molecules exhibit an inward attraction. The term also includes detergents, emulsifiers, penetrants, and wetting agents.

By "water soluble peptide" is meant a peptide having a solubility in water of at least 0.5 mg/ml, and more preferably of at least 1 mg/ml.

"Amino Acid" refers to any compound containing both an amino group and a carboxylic acid group, and includes pharmaceutically acceptable salts thereof. Although the amino group most commonly occurs at the position adjacent to the carboxy function, the amino group may be positioned at any location within the molecule. The amino acid may also contain additional functional groups, such as amino, thio, carboxyl, carboxamide, imidazole, etc. The amino acids may be synthetic or naturally occurring and may be used in either their racemic or optically active (D-, or L-) forms, for example, as a single optically active enantiomer or as any combination or ratio of enantiomers.

A "dispersing agent" refers to a component of the respirable 11-4R powder compositions described herein that is effective, when present in from 0.01 to 99 percent by weight of the composition, preferably from 0.01 to 70 percent by weight, to increase the dispersiblity of the respirable IL-4R powder compositions (determined by emitted dose determination) by at least 10% when compared to the dispersibility of the respirable IL-4R composition absent the dispersing agent.

"In-lung pulmonary bioavailability" or "relative bioavailability" is the percentage of the IL-4R administered dose which has been deposited in the lungs, and which is absorbed and becomes available in the systemic circulation of a mammal relative to the percent that is absorbed into the blood from an intramuscular or subcutaneous injection site. Representative model systems for determining in-lung bioavailabilities include rat, rabbit, and monkey. In-lung pulmonary bioavailabilities may be based upon direct intratracheal administration or by inhalation of a respirable IL-4R powder composition as described herein.

"Bulk density" refers to the density of a powder prior to compaction (i.e., the density of an uncompressed powder), and is typically measured by a well-known USP method.

"Essentially unchanged" as used in reference to monomer content or aggregate level of an IL-4R powder composition of the invention refers to a composition which exhibits a change of no more than about 2% in either monomer content or aggregate level when compared to that of the corresponding pre-spray-dried solution or suspension.

A "minimal increase" when used in reference to IL-4R aggregate level in a spray dried IL-4R powder refers to an increase in the level of aggregates of no more than about 10% in comparison to the level of aggregates in the corresponding pre-spray dried solution or suspension.

A "minimal change" when used in reference to IL-4R monomer content in a spray dried IL-4R powder refers to a change (i.e., decrease) in monomer content of no more than about 10% in comparison to the level of IL-4R monomer in the corresponding pre-spray dried solution or suspension.

"Humid condition" refers to an environment having a relative humidity greater than 30% relative humidity (RH). A particularly humid environment is one having a relative humidity greater than about 60% RH, with high humidities ranging from about 70% to 75% RH or greater.

B. Components of the Respirable IL-4R Powder Composition

The present invention provides highly dispersible respirable powder compositions containing IL-4R for pulmonary delivery thereof. The powder compositions described herein overcome many of the problems often encountered heretofore in administering peptide agents by systemic routes, particularly the problems associated with solution-based formulations of IL-4R. Examples of such problems include prolonged response time (e.g., time between administration and onset of physiological response), low systemic absorption and relatively low concentrations in tissues and secretions, the inability to maintain acceptable serum levels, and the instability of peptides, and cytokines in particular, in solution.

The compositions of the present invention are particularly effective for the treatment of allergic diseases and conditions, such as asthma and atopic dermatitis. Moreover, the spray dried IL-4R powder containing compositions described herein are surprisingly stable (i.e., exhibit minimal chemical and physical degradation upon preparation and storage, even under extreme conditions of temperature and humidity). That is to say, the powders provided herein are surprisingly robust, even in the absence of stabilizing or dispersibility enhancing excipients. The IL-4R powders of the invention (i) are readily dispersed by aerosol delivery devices (i.e., demonstrate good aerosol performance), (ii) exhibit surprisingly good physical and chemical stability during powder manufacture and processing, and upon storage, and (iii) are reproducibly prepared (Examples 1-5).

The respirable IL-4R powder compositions according to the present invention contain IL-4R, and, optionally but not necessarily, a pharmaceutically acceptable excipient. The components of the respirable IL-4R powder compositions of the invention will now be described.

IL-4R for use in the invention is generally characterized as follows. Endogenous mature interleukin-4 receptor is expressed as a 140 kDA membrane glycoprotein that binds IL-4 with high affinity (Idzerda R L et al., 1990 *J. Exp. Med.*, 171 (3), 861-873; Jacobs, C A et al. 1991, *Blood,* 77(11): 2396-2403, both of which are incorporated by reference herein). The extracellular domain of human IL-4R, cloned and produced in CHO cells in serum containing media, is a highly glycosylated (N-linked) and sialylated protein having a nonglycosylated molecular weight of 23.9 kDa and containing 209 amino acid residues. The extracellular domain IL-4R is located between residues 24 and 234 of the mature interleukin-4 receptor. Mass spectrometry data shows the protein molecular weight to be about 37 kDa, suggesting at least 35% glycosylation. By SDS-PAGE analysis, the protein elutes as a 54 kDa band. The pI of IL-4R is 3.36 to 5.18 as determined by isoelectric focusing. The unfolding transition temperature as determined by DSC is 57.8° C. and the unfolding process is highly reversible.

IL-4R for use in the compositions described herein may be purchased from a commercial source, or may be recombinantly produced, for example, using a process described in U.S. Pat. No. 5,767,065 and by Armitage et al. in *Adv Exp Med Biol* 1991; 292:121-30, both of which are incorporated by reference herein in their entirety. The IL-4R may be neutral (i.e., uncharged) or may be in the form of a pharmaceutically acceptable salt, for example, an acid addition salt such as acetate, maleate, tartrate, methanesulfonate, benzenesulfonate, toluenesulfonate, etc., or an inorganic acid salt such as hydrochloride, hydrobromide, sulfate, phosphate, etc. Cationic salts may also be employed, such as salts of sodium, potassium, calcium, magnesium, or ammonium salts.

The amount of IL-4R contained within the respirable powder compositions will be that amount necessary to pulmonarily deliver a therapeutically effective amount (i.e., amount required to exert the therapeutic effect) of IL-4R per unit dose over the course of a daily dosing regimen. In practice, this will vary depending upon the particular IL-4R (e.g., natural vs. synthetic, full-length vs. fragment and its corresponding bioactivity), the patient population, and dosing requirements. Due to the highly dispersible nature of the respirable powders of the invention, losses to the inhalation device are minimized, meaning that more of the powder dose is actually delivered to the patient. This, in turn, correlates to a lower required dosage to achieve the desired therapeutic goal.

In general, the total amount of IL-4R contained in the respirable powder compositions will range from 1 to 100% of the total weight of the respirable powder composition, preferably from 5 to 98%, more preferably from 10 to 95%, even more preferably from about 45% to 95% by weight to about 50% to about 90%. A preferred dry powder composition will contain from about 40% to 80% IL-4R (% by weight of composition), and even more preferably will contain from about 0.2% to 99% IL-4R by weight.

The effective amount of IL-4R required will vary from one patient to the next and from one therapeutic regimen to the next. The amount and frequency of administration will depend, of course, on such factors as the nature and severity of the indication being treated, the desired response, the patient population, condition of the patient, and so forth.

The generally accepted dosage appropriate for inducing a biological effect for parenterally administered sIL-4R ranges from about 1 ng/kg/day to about 10 mg/kg/day, more preferably from about 5 ug/kg/day to about 2 mg/kg/day. Such parenteral formulations of IL-4R are discussed in U.S. Pat. Nos. 5,856,296 and 6,063,371, discussed above. However, since pulmonary delivery is frequently more efficient than parenteral delivery, dosages required may vary, and in fact, may be slightly less than those utilized in parenteral formulations. Dosing of IL-4R, particularly for the treatment of allergic diseases such as asthma, is typically weekly. Weekly dosage of an IL-4R powder by inhalation can range from about 0.1 to 10 mg, more preferably between 0.5-5 mg, even more preferably between 1-2 mg. Precise dosages will depend upon various factors such as the concentration of IL-4R in the spray dried powder. Desired dosages are typically achieved in 1 to 10 breaths or 2 to 6 breaths, more preferably 1-4 breaths, depending upon the precise unit dosage form employed.

The efficiency of systemic Il-4R delivery via the method described herein, i.e., the percentage of administered dose that reaches the bloodstream (e.g., in lung pulmonary bioavailability) from a solid inhaled dosage form will typically be at least about 1%, more preferably at least about 2%, typically at least about 3-5%. In a more preferred embodiment, the efficiency of systemic delivery into the bloodstream from the lung is at least about 15% to 30%.

C. Excipients and Additives

The respirable powder compositions of the present invention may be formulated "neat" i.e. without pharmaceutical excipients or additives. This finding was particularly surprising in view of the tendency of cytokines such as IL-4R towards both degradation and aggregation. In one specific embodiment of the invention, the respirable composition is a "neat" dry powder formulation. In another embodiment, the dry powder formulation is absent particular excipients and additives, such as penetration enhancers.

Alternatively, the compositions of the invention may contain IL-4R combined with one ore more pharmaceutically acceptable excipients or additives that are suitable for respiratory and pulmonary administration. Such excipients, if present, are generally present in the powder composition in amounts ranging from about 0.01% to about 99% percent by weight, preferably from about 0.1% to about 95%, more preferably from about 0.5% to about 80%, even more preferably from about 1% to about 50-60%. Examples of excipient-containing respirable Il-4R compositions are described in Example 1. Interestingly, in the exemplary compositions described in the Examples, the presence or absence of one or more excipients did not substantially impact the chemical or physical stability of the spray dried powders of the invention, either during preparation or storage.

However, preferred excipients will, in part, serve to improve one or more of the following: the aerosol properties of the composition, its chemical stability, its physical stability, and/or storage stability. Preferred excipients may also function to provide more efficient and reproducible delivery of IL-4R by dry powder inhaler, and additionally improve the handling characteristics of the IL-4R powder composition (e.g., flowability and consistency) to facilitate manufacturing and powder filling.

In particular, the excipient materials can often function to improve the physical and chemical stability of the respirable IL-4R powder composition or active agents contained therein. For example, the excipient may minimize the residual moisture content and hinder moisture uptake and/or enhance particle size, degree of aggregation, surface properties (i.e., rugosity), ease of inhalation, and targeting of the resultant particles to the lung. The excipient(s) may also simply serve simply as bulking agents for reducing the active agent concentration in the dry powder composition.

Pharmaceutical excipients and additives useful in the present composition include, but are not limited to, proteins (i.e., large molecules composed of one or more chains of amino acids in a specific order), oligopeptides (i.e., short chains of amino acids connected by peptide bonds), peptides (i.e., a class of molecules that hydrolyze into amino acids), amino acids, lipids (i.e., fatty, waxy or oily compounds typically insoluble in water but soluble in organic solvents, containing carbon, hydrogen and, to a lesser extent, oxygen), polymers (i.e., large molecules formed by the combination of many similar smaller molecules), and carbohydrates (e.g., sugars, including monosaccharides, di-, tri-, tetra-, and oligosaccharides; derivatized sugars such as alditols, aldonic acids, esterfied sugars and the like; and plysaccharides or sugar polymers), which may be present singly or in combination. Suitable excipients include those provided in International Publication No. WO 96/32096 assigned to Inhale Therapeutic Systems, Inc., the entire contents of which are incorporated by reference herein.

Preferred excipients include sugar alcohols, lipids, DPPC, DSPC, calcium/magnesium, and hydrophobic excipients, such as hydrophobic amino acids and hydrophobic sugars. Particularly preferred excipients include zinc salts, leucine, citrate, and sugars such as raffinose. For particulate formulations, preferred excipients are those having glass transition temperatures (Tg), above about 35° C., preferably above about 45° C., more preferably above about 55° C.

Exemplary polypeptide and protein excipients include serum albumin such as human serum albumin (HSA), recombinant human albumin (rHA), gelatin, casein, hemoglobin, and the like. Particularly preferred are dispersibility enhancing polypeptides, e.g., HSA, as described in International Publication No. WO 96/32096, assigned to Inhale Therapeutic Systems, Inc., the contents of which are incorporated by reference herein.

Representative amino acid/polypeptide components, which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and peptides that function as dispersing agents. Amino acids falling into this categoray include hydrophobic amino acids such as leucine (leu), valine (val), isoleucine (isoleu), tryptophan (try) alinine (ala), methionine (met), phenylalanine (phe), tyrosine (tyr), histidine (his), and proline (pro). One particularly preferred amino acid is the amino acid leucine. Leucine, when use in the formulations described herein includes D-leucine, L-leucine, and racemic leucine. Dispersibility enhancing peptides for use in the invention include dimers, trimers, tetramers, and pentamers composed of hydrophobic amino acid components such as those described above. Examples include di-leucine, di-valine, di-isoleucine, di-tryptophan, di-alanine, and the like, tripleucine, tripvaline, tripisoleucine, triptryptophan etc.; mixed di- and tri-peptides, such as leu-val, isoleu-leu, try-ala, leu-try, etc., and leu-val-leu, val-isoleu-try, ala-leu-val, and the like and homo-tetramers or pentamers such as tetra-alanine and penta-alanine. Particularly preferred oligopeptide excipients are dimers and trimers composed of two or more leucine residues, as described in Inhale Therapeutic Systems Inc. International Patent Application PCT/US00/09785 entitled, "Dry Powder Compositions Having Improved Dispersibity. Of these, dileucine and trileucine are particularly preferred.

Another preferred feature of an excipient for use in the invention is surface activity. Surface active excipients, which may also function as dispering agents, such as hydrophobic amino acids (e.g., leu, val isoleu, phe, etc.), di- and tri-peptides, polyamino acids (e.g., polyglutamic acid) and proteins (e.g., HSA, rHA, hemoglobin gelatin) are particularly preferred, since due to their surface active nature, these excipients tend to concentrate on the surface of the particles of the respirable IL-4R composition, making the resultant particles highly dispersible in nature. Other exemplary surface active agents that may be included in the respirable IL-4R compositions described herein include but are not limited to polysorbates, lecithin, oleic acid, benzalkonium chloride, and sorbitan esters.

Carbohydrate excipients suitable for use in the invention include, for example, monosaccharides such as fructose, maltose, galactose, glucose, d-mannose, sorbose, and the like; disaccharides, such as raffinose, melezitose, maltodestrins, dextrans, straches and the like; and alditols, such asmannitol, xylitol, maltitol, lactitol, xylitol sorbital (glucito), myoinasitol and the like.

The respirable IL-4R compositions may also include a buffer or a pH adjusting agent; typically, the buffer is a salt prepared from an organic acid or base. Representative buffers include organic acid salts such as salts of citric acid, ascorbic acid, gluconic acid, carbonic acid, taratric acid, succinic acid, acetic acid, or phthalic acid, Tris, tromethamine hydrochloride, or phosphate buffer.

Additionally, the respirable IL-4R composition of the invention may include polymeric excipients/additives such as polyvinylpyrrolidones, derivatized celluloses such as hydroxypropylmethylcellulose, Ficcols (a polymeric sugar), hydroxyethylsartch, dextrates (e.g., cyclodextrins, such as 2-hydroxypropyl-β-cyclodextrin and sulfobutylether-β-cyclodextrin), polyethylene glycols, pectin flavoring agents, salts (e.g., sodium chloride), antimicrobial agents, sweeteners, antioxidants, antistatic agents, surfactants (e.g., polysorbates such as "TWEEN 20" and "TWEEN 80"), lecithin, oleic acid, benzalkonium chloride, sorbitan esters, lipids (e.g., phospholipids, fatty acids), steroids (e.g. cholesterol) and chelating agents (e.g., EDTA). For compositions containing a polymeric component, the polymer is typically present to a limited extent in the composition, i.e., at levels less than about 10% by weight. Preferred compositions of the invention are those in which the IL-4R is preferably non-liposomally or polymer encapsulated, or non-coated (i.e., absent a discrete coating layer). Preferred IL-4R compositions such as those exemplified herein are immediate-acting formulations, i.e., designed for immediate rather than for sustained release applications.

Other pharmaceutical excipients and/or additives suitable for use in the respirable IL-4R compositions according to the invention are listed in "Remington: the Science & Practice of Pharmacy", $19^{th}$ ed., Williams & Williams, (1995, in the "Physician's Desk Reference", $52^{nd}$ ed., Medical Economics, Montvale, N.J. (1998), and in "The Handbook of Pharmaceutical Excipients", $3^{rd}$ Edition, A. H. Kibbe, ed., American Pharmaceutical Association, Pharmaceutical Press, 2000, the disclosures of which are herein incorporated by reference.

In accordance with the invention, the respirable IL-4R powder composition may be a dry powder, the dry powder being crystalline, an amorphous glass, or a mixture of both forms. For formulations containing a surface active agent, the surface active material (in either crystalline or amorphous form), will typical be present on the surface of the particles in a higher concentration than in the bulk powder.

D. Preparing the Respirable Il-4R Compositions

Respirable Il-4R powder compositions, such as dry powder formulations are preferably prepared by spray-drying. Spray-drying of the formulations is carried out, for example, as described generally in the "Spray-drying Handbook", $5^{th}$ ed., K. masters, John Wiley & Sons, Inc., NY, N.Y. (1991), in Platz, R., et al., International Patent Publication Nos. WO 97/41833 (1997) and WO 96/32149 (1996), the contents of which are incorporated herein by reference.

To prepare an IL-4R solution for spray-drying, IL-4R (and any other exipients) is generally dissolved in water, optionally containing a physiologically acceptable buffer. The pH range of solution is generally between about 3 and 10, which nearer neutral pHs being preferred, since such pHs may aid in maintaining the physiological compatibility of the powder after dissolution of powder within the lung. The aqueous formulation may optionally contain additional water-miscible solvents, such as acetone, alcohols and the like. Representative alcohols are lower alcohols such as methanol, ethanol, propanol, isopropanol, and the like. The solutions will generally contain IL-4R dissolved at a concentration from 0.01% (weight/volume) to about 20% (weight/volume), preferably from 0.1% to 10% (weight/volume), more preferably 1% to 3% (weight/volume). Alternatively, components of the IL-4R formulation may be spray-dried using an organic solvent or co-solvent system, employing one or more solvents such as acetone, alcohols (e.g., methanol and ethanol), ethers, aldehydes, hydrocarbons, ketones and polar aprotic solvents.

The IL-4R containing solutions are then spray dried in a conventional spray drier, such as those available from commercial suppliers such as Niro A/S (Denmark), Buchi (Switzerland) and the like, resulting in a dispersible, respirable IL-4R composition, preferably in the form of a respirable dry powder. Optimal conditions for spray-drying the active agent solutions will vary depending upon the formulation components, and are generally determined experimentally. The gas used to spray-dry the material is typically air, although inert gases such as nitrogen or argon are also suitable. Moreover, the temperature of both the inlet and outlet of the gas used to dry the sprayed material is such that it does not cause decomposition of the IL-4R in the sprayed material. Such temperatures are typically determined experimentally, although generally, the inlet temperature will range from about 50° C. to about 200° C. while the outlet temperature will range from about 30° C. to about 150° C.

The preparation of respirable, dry IL-4R powder compositions under a variety of spray-drying process parameters are described in Examples 1 and 2. Surprisingly, the shear forces produced by atomization of the solution during spray-drying do not result in hydrolysis or aggregation of IL-4R. As described herein, highly dispersible dry powders having good physical and chemical stability and good aerodynamic properties can be prepared reproducibly and under a variety of process conditions.

Alternatively, although less preferably, the respirable IL-4R powder compositions may be prepared by lyophilization, vacuum drying, spray freeze drying, super critical fluid processing, air drying, or other forms of evaporative drying.

In some instances, it may be desirable to provide the respirable IL-4R dry powder formulation in a form that possesses improved handling/processing characteristics, e.g., reduced static, better flowability, low caking and the like, by preparing compositions composed of fine particle aggregates, that is, aggregates or agglomerates of the above-described respirable IL-4R. Dry powder particles, where the aggregates are readily broken back down to the fine powder components for pulmonary delivery, as described, e.g., in Johnson, K., et al., U.S. Pat. No. 5,654,007, 1997, incorporated herein by reference. Alternatively, the respirable IL-4R powders may be prepared by agglomerating the powder components, sieving the materials to obtain the agglomerates, spheronizing to provide a more spherical agglomerate, and sizing to obtain a uniformly-sized product, as described, e.g., in Ahlneck, C., et al. International PCT Publication No. WO 95/09616 (1995), incorporated herein by reference.

The respirable IL-4R dry powders are preferably maintained under dry (i.e., relatively low humidity) conditions during manufacture, processing, and storage. Irrespective of the drying process employed, the process will preferably result in respirable highly dispersible compositions composed of substantially amorphous IL-4R particles.

E. Characteristics of the Respirable IL-4R Powder Compositions

Certain physical characteristics of the spray dried IL-4R powder compositions are preferred to maximize the efficiency of aerosolized delivery of such compositions to the lung.

The respirable IL-4R powder compositions are composed of particles effective to penetrate into the lungs. Passage of the particles into the lung physiology is an important aspect of the present invention. To this end, the particles of the invention have a mass median diameter (MMD) of less than about 10 µm, preferably less than 7.5 µm, and more preferably less than 5 µm, and usually are in the range of 0.1 µm to 5 µm in diameter. Preferred compositions are composed of particles having and MMD from about 0.5 to 3.5 µm. Examples of respirable IL-4R powder compositions of varying concentrations of active agent(s) and/or excipient are described in Example 1. The respirable IL-4R powder compositions may also contain non-respirable carrier particles such as lactose, where the non-respirable particles are typically greater than about 40 microns in size. In a preferred embodiment, the dry powder is non-liposomal or non-lipid containing.

The respirable IL-4R powder compositions of the invention are further characterized by an aerosol particle size distribution less than about 10 µm mass median aerodynamic diameter (MMAD), preferably less than 5.0 µm, and more preferably less than 3.5 µm. The mass median aerodynamic diameters of the powders will characteristically range from about 0.5-10 µm, preferably from about 0.5-5.0 µm MMAD, more preferably from about 1.0-4.0 µm MMAD, and even more preferably from about 1.5 to 3.5 µm.

The respirable IL-4R powder compositions, particularly the respirable dry powder compositions, generally have a moisture content below about 10% by weight, usually below about 5% by weight, and preferably below about 3% by weight. Such low moisture-containing solids tend to exhibit a greater stability upon packaging and storage.

The dry powders preferably have a bulk density ranging from about 0.1-10 g/cc, preferably from about 0.25-4 g/cc, more preferably from about 0.5-2 g/cc, and most preferably from about 0.7-1.4 g/cc.

The emitted dose (ED) of these powders is greater than 30% and usually greater than 40%. More preferably, the ED of the powders of the invention is greater than 50%, and is often greater than 55%.

An additional measure for characterizing the overall aerosol performance of a dry powder is the fine particle dose (FPD) or fine particle fraction (FPF), which describes the mass percentage of powder having an aerodynamic diameter less than 3.3 microns. Dry powders having an FPF value greater than 40%, more preferably greater than 50%, even more preferably greater than 60% are particularly well suited for pulmonary delivery. Powders containing at least fifty percent of aerosol particles sized between 0.5 and 3.5 µm are extremely effective when delivered in aerosolized form, in reaching the regions of the lung, including the alveoli.

The spray dried respirable IL-4R powder compositions of the present invention are further characterized as having an essentially unchanged monomer content as compared to that of its pre-spray dried solution or suspension. In other words, the spray drying process does not induce the formation of dimers or other aggregates, thereby affecting the percent monomer in the composition. That is to say, the change in monomer content between spray dried powder and pre-spray dried solution or suspension is "essentially unchanged", e.g., the percentage of monomer content of spray dried powder as compared to that of the pre-spray dried solution or suspension is preferably no more than about 15%, more preferably no more than about 10%, more preferably no more than about 7%, even more preferably about 5% or less, as exemplified by the representative IL-4R powders described in the Examples.

The spray dried respirable IL-4R powder compositions of the present invention are "storage stable", i.e., characterized by minimal insoluble aggregate formation and/or a minimal decrease in monomer content, when stored for extended periods at extreme temperatures ("temperature stable") and humidities ("moisture stable"). For example, the spray dried respirable IL-4R powder compositions of the present invention experience minimal aggregate formation and minimal decrease in monomer content after storage for a period of time (e.g., two weeks or more) at a temperature ranging from about 2° C. to about 50° C., preferably about 25° C., and/or a relative humidity ranging from 0% to about 75%, preferably about 33% RH. Specifically, the stored spray dried respirable IL-4R powder compositions of the present invention preferably form less than about 15% insoluble aggregates (as compared to the pre-spray dried solutions or suspensions), more preferably less than about 10% insoluble aggregates, more preferably less than about 7% insoluble aggregates, even more preferably about 5% or less insoluble aggregates. Alternatively, the stored spray dried respirable IL-4R powder compositions of the present invention preferably experience a decrease in monomer content that is no more than about 20%, preferably no more than about 10%, more preferably no more than about 7%, even more preferably about 5% or less.

It is important to note the distinctions between respirable powder-based formulations and nebulized formulations. Despite the fact that nebulized formulations may be considered by some to be "inhaleable", in that they are breathed through the mouth and into the lungs, they are not "respirable" as defined herein. For example, nebulized formulations typically cannot reach the tissues of the deep lung and be absorbed through the epithelial cells therein into blood circulation. Moreover nebulized formulations are solution-based, i.e., are administered in solution rather than in solid form.

Representative respirable IL-4R powder compositions for pulmonary delivery are provided in Examples 1-5.

F. Pulmonary Administration of the Respirable IL-4R Powder Compositions

The respirable IL-4R powder compositions, particularly the dry powder compositions described herein, are preferably delivered using any suitable dry powder inhaler (DPI), i.e., an inhaler device that utilizes the patient's inhaled breath as a vehicle to transport the previously dispersed (by passive or active means) dry powder to the lungs. Preferred are Inhale Therapeutic Systems' dry powder inhalation devices as described in Patton, J. S., et al., U.S. Pat. No. 5,458,135 (1995); Smith, A., et al., U.S. Pat. No. 5,740,794, (1998); Smith A., et al., U.S. Pat. No. 5,785,049(1998), and in International Patent application PCT 00/18084.

When administered using a device of this type, the respirable IL-4R powder composition is contained in a receptacle having a puncturable lid or other access surface, preferably a blister package or cartridge, where the receptacle may contain a single dosage unit or multiple dosage units. Large numbers of cavities are conveniently filled with metered doses of dry powder medicament as described in Parks, D. J. et al., International Patent Publication WO 97/41031 (1997).

Also suitable for delivering the respirable IL-4R powder formulations described herein are dry powder inhalers of the type described, for example, in Cocozza, S., U.S. Pat. No. 3,906,950 (1974), and Cocozza, S., U.S. Pat. No. 4,013,075, (1977), wherein a premeasured dose of dry powder for delivery to a subject is contained within a hard gelatin capsule.

Other dry powder dispersion devices for pulmonary administration of dry powders include those described, for example, in Newell, R. E. et al., European Patent No. EP 129985, (1988); in Hodson, P. D. et al., European Patent No. EP 472598, (1996); in Cocozza, S., et al., European Patent No. EP 467172, (1994), and in Lloyd, L. J. et al., U.S. Pat. No. 5,522,385, (1996). Also suitable for delivering the IL-4R powder compositions of the invention are inhalation devices such as the Astra-Draco "TURBUHALER". This type of device is described in detail in Virtanen, R., U.S. Pat. No. 4,668,218); in Wetterlin, K. et al., U.S. Pat. No. 4,667,668, (1987); and in Wetterlin K., et al., U.S. Pat. No. 4,805,811, (1989). Also suitable are devices which employ the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device, such as described in Mulhauser, P., et al., U.S. Pat. No. 5,388,572, (1997).

The inhaleable IL-4R powder compositions may also be delivered using a pressurized, metered dose inhaler (MDI) containing solution or suspension of drug in a pharmaceutically inert liquid propellant, e.g., a chlorofluorocarbon or fluorocarbon, as described in Laube, et al., U.S. Pat. No. 5,320,094, (1994), and in Rubsamen, R. M. et al., U.S. Pat. No. 5,672,581 (1994). Prior to use, the respirable IL-4R powder compositions are generally stored in a receptacle under ambient conditions, and preferably are stored at temperatures at or below about 25° C., and relative humidities (RH) ranging from about 30 to 60%. More preferred relative humidity conditions, e.g., less than about 30% may be achieved by the incorporation of desiccating agent in the secondary packaging of the dosage form. The respirable dry powders of the invention are characterized not only by good aerosol performance, but by good stability, as well.

When aerosolized for direct delivery to the lung, the IL-4R powder compositions described herein will exhibit good in-lung bioavailabilities.

G. Utility

The respirable IL-4R powder compositions of the invention, when administered pulmonarily, are particularly effective in the treatment of allergic diseases and disorders, such as asthma, atopy, atopic dermititis, and other conditions associated with high serum levels of IgE and $IgG_1$.

The respirable IL-4R powder compositions can also be used for treating or preventing allergic, viral, parasitic, and bacterial diseases and mildew infectious diseases, particularly when administered in combination with γ-interferon. (See European Patent No. EP 585,681 (1994)).

The inventive powder compositions, when inhaled, penetrate into the airways of the lungs, enter the circulatory system and achieve effective systemic delivery. Moreover, the doses of IL-4R powder administered pulmonarily are typically much less than those administered orally due to the loss associated with digestion and degradation for oral dosage forms.

The respirable IL-4R powder compositions of the present invention find utility as alternates or adjuncts to current asthma therapies.

The respirable IL-4R powder compositions find particular utility in the physiological regulation of serum levels of IL-4 and immunoglobulins associated therewith (e.g., IgE, and $IgG_1$).

The respirable IL-4R powder compositions find further utility as enhancers of the biological activity of the cytokine IL-4, thereby allowing for the reduction in cytokine dosage required and the minimization of negative side effects associated therewith (See U.S. Pat. No. 6,063,371, incorporated by reference herein).

The following examples illustrate, but in no way are intended to limit the scope of the present invention.

EXAMPLES

Materials and Methods
The following materials were used in the examples below

Materials
L-Leucine (Aldrich, St. Louis, Mo.)
Hydrochloric Acid (J. T. Baker, Phillipsburg, N.J.)
Sodium Hydroxide 0.1N Volumetric Solution (J. T. Baker, Phillipsburg, N.J.)
Ethanol, 200 proof (USP/NF, Spectrum Chemical Mfg. Corp., New Brunswick, N.J.)
Methanol (HPLC grade, EM Industries, Gibbstown, N.J.)
Recombinant Human IL-4R (rhuIL-4R) (Immunex Corporation, Seattle, Wash.)
Male Sprague Dawley Rats (Simonsen laboratories, Gilroy, Calif.)

Powder Analysis
IL-4R Solutions: The following solutions of IL-4R were prepared. Solution A contained 22.6 mg/mL of serum free IL-4R in 5 mM $NaH_2PO_4$ buffered to a pH of 7.0. Solution B contained 6.1 mg/mL of serum free IL-4R in distilled water. The solution concentrations are expressed as mass of peptide per unit volume. Values reported herein are from amino acid analysis data; values from UV testing were slightly higher (25.6 and 7.8 mg. mL, respectively).

Particle Size. The particle size distribution of the exemplary IL-4R powders was measured by liquid centrifugal sedimentation in a Horiba CAPA-700 Particle Size Analyzer following dispersion of the powders in SediSperse A-11 (Micrometrics, Norcross, Ga.).

Moisture Content. The moisture content of the powders was measured by the Karl Fischer Titrimetric technique using a Mitsubishi CA-06 Moisture Meter or by thermogravimetric analysis.

MMADs. The aerosol particle size distribution (MMAD) was determined using a cascade impactor (Graseby Andersen, Smyrna, Ga.) at a flow rate of 28 L/min, ignoring powder loss of the inlet manifold.

Emitted Dose. Emitted doses were determined as described in the "Definitions" section using an Inhale dry powder inhaler as described in U.S. Pat. No. 5,740,794 and a Gelman glass filter, 47 mm diameter.

Scanning Electron Microscopy (SEM). Particle morphology was determined using an XL 30 ESEM manufactured by Philips Electron Optics (Eindhoven, The Netherlands).

Thermal Analyses. Thermal analysis experiments were conducted using a modulated Differntial Scanning Calorimeter (mDSC-Model 2920) Dielectric Analyzer (DEA 2970) and a Thermal Gravimetric Analyzer (TGA Model 2950 manufactured by TA Instruments (New Castle, Del.). Hot stage microscopy was conducted using a Nikon Optiphot-2-pol optical microscope (Nikon Inc., Torrance, Calif.), a Hamatsu camera and C2400 controller (Hamatsu Photonics, herrsching, German7), a Mettler-Toledo FP90 central processor (Mettler-Toledo, Columbus, Ohio) and FP8902H hot stage attachment (Mettler, Toledo, Ohio).

Chemical Characterization: SE-HPLC experiments were run on a Waters HPLC Alliance model 2690 system (Alliance HPLC Systems, Millford, Mass.) running Millenium V software (Waters). Chromatography columns were obtained from Phenomenex (Torrance, Calif.). UV experiments were performed on a Hitachi U-3000, dual beam spectrophotometer (Hitachi Instruments Inc., San Jose, Calif.). SDS-PAGW experiments were performed on Novex Xcell electrophoreses unit (Novex, San Diego, Calif.).

Example 1

Preparation of IL-4R Dry Powders

Storage stable spray-dried powders of the interleukin receptor protein, IL-4R, having superior aerosol properties and further characterized by superior chemical and physical stabilities were prepared. Powders were prepared in both the presence and absence of excipients; excipients employed were from a variety of representative chemical classes (e.g., organic acid salts, amino acids, metal cations). The IL-4R powders are stable upon long-term storage and are resistance to extreme conditions of temperature and humidity.

Representative IL-4R powders were prepared according to the following protocols.

Example 1 (A)—Neat Formulation of IL-4R

Dry powder compositions of IL-4R were formulated in deionized water without added excipients for spray-drying. 600-700 mg batches of the neat formulation of IL-4R were prepared by spray drying an appropriate volume of Solution A. The final concentration of phosphate buffer in the pre-spray dried solution was 1.9 mM.

Example 1 (B)—Zinc Chloride Containing Formulation of IL-4R

Dry powder compositions of IL-4R were formulated in deionized water with zinc chloride for spray-drying. 600-700 mg batches of a 5.4:1 $ZnCl_2$: IL-4R formulations were prepared by dispensing 19.53 mL of IL-4R Solution A and 0.456 mL of a 19.37 mg/mL solution of $ZnCl_2$ into a 50 mL volumetric flask and adjusting the final volume to 50 mL by addition of deionized water. The final concentration of phosphate buffer was 1.9 mM.

Example 1(C)—Citrate Containing Formulation of IL-4R

Dry powder compositions of IL-4R were formulated in deionized water containing a citrate salt for spray-drying. 600-700 mg batches of citrate: IL-4R formulations were prepared by combining approximately 12 mL of Solution A and 200 mg of citrate in solution at pH 7.5 and adjusting to a final volume of 50 mL by addition of deionized water. The final concentration of phosphate buffer was 1.2 mM.

Example 1(D)—Leucine Containing Formulation of IL-4R

Dry powder compositions of IL-4R were formulated in deionized water containing leucine for spray-drying. 600-700 mg batches of the leucine: IL-4R formulations were prepared by combining approximately 12 mL of Solution A and 200 mg of leucine and adjusting to a final volume of 50 mL by addition of deionized water. The final concentration of phosphate buffer was 1.2 mM and the pH was 7.5.

Relative Amounts of Components (wt/wt) in Formulations 1(A)-1(D) are summarized in Table 1 below.

TABLE 1

Formulations of IL-4R

| Formulation | IL-4R % | Phosphate % | $ZnCl_2$ % | Citrate % | Leucine % |
|---|---|---|---|---|---|
| Neat IL-4R | 98.0 | 2.0 | 0.0 | 0.0 | 0.0 |
| 5.4:1 Zn:IL4R | 96.9 | 1.9 | 1.2 | 0.0 | 0.0 |
| Citrate:IL-4R | 66.3 | 1.3 | 0.0 | 32.4 | 0.0 |
| Leucine:IL-4R | 66.3 | 1.3 | 0.0 | 0.0 | 32.4 |

Additional powder formulations contemplated include IL-4R formulations, both neat and excipient containing, prepared using a citrate buffered or a water-based (no buffer) IL-4R solution. Preferred IL-4R powders in accordance with the invention comprise, in addition to IL-4R, one or more of the following excipients: trileucine, raffinose, mannitol, sucrose, F-68, divalent metal cations such as magnesium, calcium, and the like, glucophosphate, zinc salts, trehalose, glycine and histidine. Specific formulations may comprise from 10-40 weight % trileucine, or 1% by weight F-68, or 10% by weight citrate, or 3:1 to 10:1 by weight cationic divalent metal cation: IL-4R, or 10-30% by weight sucrose, or 5-50% by weight trehalose, or any combination of the above. Additional illustrative IL-4R formulations include those containing both citrate and leucine (e.g., a formulation with a citrate: leucine: IL-4R ratio of 15:15:70) or raffinose (e.g., formulations comprising 5%-50% raffinose).

The above IL-4R formulations above were spray dried using a laboratory scale Buchi mini spray-dryer (Buchi Labortechnik, Ag., Meierseggstrasse, Switzerland) fitted with a modified cyclone, an atomizer nozzle and a powder collection vessel. The atomizer of the Buchi spray dryer was operated with clean dry air. The liquid flow rate into the Buchi was 5 mL/min. The inlet temperature was adjusted to achieve the target particle size and morphology (80° C. to 150° C.). The outlet temperature ranged from about 30° C. to 100° C. Yields were greater than 75% ranging from 78-91% for the IL-4R formulation lots 1(A)-1(D). The IL-4R powders (3±0.15 mg) were transferred into a glovebox with a relative humidity less than 5% and placed into unit dosage forms (blister packs, BP's) suitable for use in a dry powder inhaler device as described in U.S. Pat. No. 5,740,794. Evaluation and characterization of the resulting solids is described below.

Example 2

Stability of IL-4R Powder Formulations

The purpose of the studies of Examples 2-5 was to evaluate aerosol performance, physical, and chemical stability of the representative IL-4R dry powder formulations described in Example 1. Aerosol, thermal, physical, and chemical tests were performed on the powders as initially prepared. Thermal and physical and chemical analyses were also performed after 2 weeks storage at four different temperatures (2-8° C., 25° C., 40° C. and 50° C.) and 3 relative humidities at 25° C. (0, 33 and 75%). The stability protocol is set forth below:

Powders were filled into foil/PVC blister packs and assayed for emitted dose, particle size distributions and thermal analyses at initial time points only. Chemical characterization and SEM analyses were performed on bulk aerosol drug powders (i.e., not contained in blister packs) at initial and 2 week timepoints. All powders were handled in humidity-controlled glove boxes with a relative humidity of less than 5%.

Bulk powder was weighed into borosilicate glass vials in a glove box. For 0% relative humidity (RH) stability samples, vials were capped, placed into a foil overwrap pouch containing desiccant and heat-sealed before storing in temperature chambers. For humidity controlled stability samples, vials were left open and stored in desiccators at 25° C. Samples were pulled and analyzed by UV, SDS-PAGE, SE-HPLC and SEM after 2 weeks.

TABLE 2

Summary of Stability Protocol for IL-4R Spray Dried Bulk Powders and Stock Solutions

| | | Testing Conditions | | | | | |
| | | 2 Weeks[3] | | | | | |
| Test | Initial | 2-8° C./ 0%/RH | 25° C./ 0%/RH | 25° C./ 33%/RH | 25° C./ 75%/RH | 40° C./ 0%/RH | 50° C./ 0%/RH |
|---|---|---|---|---|---|---|---|
| DDE[1] | X | | | | | | |
| MMAD[1] | X | | | | | | |
| DSC[1] | X | | | | | | |
| TGA[1] | X | | | | | | |
| UV[2] | X | X | X | X | X | X | X |
| SE-HPLC[2] | X | X | X | X | X | X | X |
| SDS-PAGE[2] | X | X | X | X | X | X | X |
| SEM | X[1] | X[2] | X[2] | X[2] | X[2] | X[2] | X[2] |

[1]test performed using blister packs
[2]test performed using bulk powder
[3]bulk aerosol powder stored in borosilicate glass vials capped and parafilmed in a sealed foil overwrap
4 bulk aerosol powder stored in borosilicate glass vials with caps off

TABLE 3

Aqueous Dilutions from Stock

| Test | Initial[5] | Testing Conditions 2 Weeks[6] | |
|---|---|---|---|
| | | 25° C. | 50° C. |
| UV | X | X | X |
| SE-HPLC | X | X | X |
| ASA-PFW | X | X | X |

[5]solution diluted with water from IL-4R Solution A
[6]1 mL of a 1 mg/mL IL-4R solution stored in borosilicate glass vials capped and parafilmed in a sealed foil overwrap Example 3

Aerosol Performance of IL-4R Powder Formulations

Aerosol tests were performed using a dry powder inhaler as described in U.S. Pat. No. 5,740,794, assigned to Inhale Therapeutic Systems Inc. All of the filled blister packs were stored in a dry box prior to use for aerosol testing.

Example 3(A): Emitted Dose

The emitted dose was measured by collecting the aerosol on a glass fiber filter placed in a holder over the mouthpiece of the chamber of the device. To measure the emitted dose percent (ED %), a blister pack was dispersed as an aerosol using a dry powder inhaler as described above. The powder sample was collected on a pre-weighed glass fiber filter (Gelman, 47 mm diameter). The aerosol cloud was collected onto the filter from the chamber by drawing at an airflow rate of 30±0.5 L/min for 2.5-3.5 seconds. An automatic timer controlled the duration of the draw. The sampling pattern simulates a patient's slow deep inspiration.

The ED % was calculated by dividing the mass of the powder collected on the filter by the mass of powder in the blister pack (actual mass). Results are reported in Table 4. Each result reported was the average and standard deviation of 10 measurements.

Example 3(B): Mass Median Aerodynamic Diameter (MMAD) and Geometric Standard Deviation (GSD)

Mass Median aerodynamic diameter and particle size distribution of the aerosol were obtained using an 8-stage (9.0, 5.8, 4.7, 3.3, 2.1, 1.1, 0.7, and 0.4 μm cut sizes) Andersen Cascade Impactor. Each Andersen measurement was obtained by dispersing 10 blister packs of 3 mg fill weight in a dry powder inhaler while pulling a vacuum at 28.3±0.5 L/min for 2.5 seconds. An automatic timer controlled the duration of the draw. From this data a mass median aerodynamic diameter was calculated. Results are set forth in Table 4.

Geometric standard deviations (GSD's) were calculated graphically from the Andersen MMAD data. The plate cut-off diameter was plotted as a function of the cumulative percent undersize on a probability scale. The GSD was taken as the diameter at 85% divided by the diameter at 50%. Values obtained are listed in Table 4.

Example 3(C): Fine Particle Fraction (FPF)

The $FPF_{\%<3.3 \mu m}$ was obtained by using the Andersen cascade impactor stages F and 3 in short stake set up. Each FPF measurement was obtained by dispersing 2 blister packs of 3 mg fill weight in a dry powder inhaler while pulling a vacuum at 28.3 L/min for 2.5 seconds. Results are set forth in Table 4.

TABLE 4

Initial Aerosol Test Results for IL-4R Formulations (3 mg fill weight)

| Formulation | Lot # | Wt % IL-4R | MMAD (μm) | Emitted Dose (%) | FPF (% <3.3 μm) | GSD (μm) |
|---|---|---|---|---|---|---|
| Neat IL-4R | NM1392-04 | 98.0 | 3.9 | 59.6 (0.12)** | 0.43(21)* | 1.6 |
| 7:1 Zn:IL-4R | NM1392-05 | 96.9 | 4.0 | 68.6 (0.040)** | 0.34(0)* | 1.6 |
| Citrate:IL-4R | NM1392-06 | 66.3 | 3.7 | 63.4 (0.09)** | 0.35(2)* | 1.7 |
| Leucine:IL-4R | NM1392-07 | 66.3 | 2.9 | 75.9 (0.08)** | 0.56(6) | 2.1 |

*RSD for n = 3
**Values are the mean and RSD, in parentheses, of 10 measurements.

The aerosol performance of the IL-4R powder formulations was quite good, all having ED values of essentially 60% or greater and MMAD values of 4 μm or less, with at least 34% or particle having MMADs of less than 3.3 μm.

The GSD values were all less than 2 μm, except for the leucine formulation. This was believed to be an artifact due to the observed bi-modal particle size distribution generated from the Andersen CI.

Example 4

Solid State Characterization of IL-4R Powder Formulations

Example 4(A)—Scanning Electron Microscopy

Scanning electron microscopy was utilized to obtain initial morphological information on the spray-dried powders and to assess changes in morphology upon storage under varying conditions of temperature and humidity.

Images were taken with a Philips XL30 ESEM operated in high vacuum mode using a Everhart-Thornley detector to capture secondary electrons for the image composition. Accelerating voltages were 3 to 10 kV using a $LaB_6$ source. Working distances ranged from 30 to 10 μm.

All powders with the exception of the leucine:IL-4R powder, Formulation 1(D), exhibited no appreciable change in morphology after 2 weeks storage at the temperature and RH condition described in the stability protocol of Example 2 (Table 2). Some of the leucine:IL-4R powders exhibited morphological changes at RH values at 33 to 75% RH as well as at temperatures of 40 to 50° C., characterized by ribbon-like growths which may be due to crystallization of amorphous leucine.

When examined visually by SEM, the particles may exhibit a wrinkled, raisin-like morphology. Rugose particles (i.e., deep wrinkled particles that are substantially more rough than smooth) are most preferred.

The effects of temperature and relative humidity for representative IL-4R formulations was determined. Of the illustrative IL-4R powders prepared, the leucine spray dried powder appeared to be the least morphologically stable, based upon temperature and RH-driven changes in morphology. No significant morphology changes were noted in any of the other powders when exposed to identical storage conditions.

Example 4(B)—Thermal Analysis

Differential Scanning Calormiety (DSC): DSC profiles were generated by heating a sample in hermetically sealed pan in a TA Instruments DSC. Sample weights were on the order of 3.5-4.5 mg. The DSC heating rate was 10° C./min with helium as the purge gas. The temperature was initially ramped to 70° C., cooled at 10° C./min to −30° C., and reheating at 10° C./min to 220° C. in order to remove thermal history instead of using modulation mode. All of the powders exhibited a large endotherm at approximately 198° C. The zinc containing IL-4R formulation, Formulation 1(B), exhibited an additional endotherm at about 180° C. The citrate containing IL-4R formulation, Formulation 1(C), exhibited an additional endotherm at about 172° C. The leucine containing IL-4R formulation, Formulation 1(D), exhibited an additional endotherm at about 186° C. No glass transition (Tg) was noted for the powders using this technique.

Thus, the spray dried powders of the invention exhibit glass transition temperatures that are much higher than room temperature, a preferred characteristic of dry powder formulations, particularly for long-term storage. Thus, in another aspect, the representative IL-4R powders of the invention are characterized by Tgs that are higher than 100° C. Due to the high Tgs of the powders of the invention, these IL-4R powders can be stably stored at temperatures in excess of ambient or 25° C., and can be stably stored at 30° C., 35° C., 40° C., 45° C., 50° C., 55° C., 60° C., 65° C. or greater (up to about 100° C. or even more) for extended periods of time (e.g., one week, two weeks, one month, two months, three to six months, nine months, up to a year or longer), whilst maintaining their advantageous aerosol characteristics (exhibiting essentially minimal drop in emitted dose, of no more than about 15%, preferably no more than about 10%, and even more preferably no more than about 5%, and essentially no change in MMAD, as characterized by an increase in MMAD of no more than about 1 micron, and preferably no more than about 0.75 microns, and even more preferably no more than about 0.5 microns, upon storage).

Dielectric Relazation Spectrometry (DRS): Sine the glass transition temperature (Tg) of the IL-4R spray dried formulations could not be determined by DSC, DRS was performed. Two DRS experiments were conducted on the zinc containing IL-4R formulation, Formulation 1(B), to better identify the glass transition temperature of a representative formulation. The first experiment conducted was a standard DRS analysis (TA Instruments Dieletctic Analyzer (DEA 2970)), run at 2° C./min from 30° C. to 150° C. and cooled to 30° C. again, scanning through frequencies of 1, 10, 100, $10^3$, and $10^4$ and $10^5$ Hz. The second experiment conducted was a softening experiment much like a thermal mechanical analyzer (TMA) run at 2° C./min from 30° C. to 250° C. and scanning through frequencies of 1, 10, 100, $10^3$, and $10^4$ and $10^5$ Hz. Both experiments were run on the Zn:IL-4R powder as is (Formulation 1(B)) and after drying overnight at 100° C. (Formulation 1(B)-(D).

From these studies, it was concluded that there is no glass transition below the decomposition temperature for the dried sample and no glass transition below 150° C. for the undried sample. This indicates that the changes in the baseline below 100° C. observed by DSC were not due to a glass transition event. Thus, the Tg of this formulation is greater than the decomposition temperature of the protein.

Thermo mechanical Analysis (TMA): The TMA experiments were performed by monitoring sample thickness during a DRS experiment. The same electrode configuration was used as in the first experiment, except the gasket was removed. The ram force was set at 20N and the thickness of the sample and the temperature were recorded manually every couple of minutes from 30° C. to 250° C. The onset of softening is at 224° C. for both Formulation 1 (B) and Formulation 1 (B)-D. The softening seen in the TMA experiments is due to degradation and a possibility of a glass transition happening simultaneously. Since there is no other softening happening at lower temperatures, the 1 Hz peaks from the standard DRS tests are due to another mechanism such as the onset of side chain motions or ion conduction and not due to a glass transition (Seyler, R. J., 1994, "Assignment of the Glass Transition", *ASTM*, 108-113). If the glass transition happens simultaneously with the decomposition, then in the sample with the lower 1 Hz loss factor peak may have the glass transition shifted to a lower temperature as well. Since the standard DEA test was only run to 150° C., it is clear that there is no glass transition below 150° C. Evaluation of the permitivity versus temperature plots confirmed the standard s-shaped profiles expected for this type of analysis.

Therman Gravimetric Analysis (TGA): The residual solvent content in the powder after spray drying was determined by TGA using a TA Instruments TGA. Approximately 3 mg of powder was packed into a hermetically sealed aluminum pan in a glovebox at a relative humidity less than 3%. The TGA was zeroed without the pan and the weight of the powder was recorded in the comment section. Just prior to analysis the pan was punctured with a pin and loaded into the equipment. The scan rate was 10° C./min from 25-175° C. The results are shown in Table 5.

TABLE 5

Solvent Content by TGA of IL-4R Spray Dried Powders

| Formulation | Lot # | Weight % Solvent |
| --- | --- | --- |
| Neat IL-4R | NM1392-04 | 2.9 |
| 7:1 Zn:IL-4R | NM1392-05 | 3.2 |
| Citrate:IL-4R | NM1392-06 | 3.9 |
| Leucine:IL-4R | NM1392-07 | 2.4 |

Hot Stage Microscopy (HSM): Hot stage microscopy was conducted from room temperature to 220° C. using a Nikon Optiphot-2-pol optical microscope, a Hamatsu camera and C2400 controller, a Mettler Toledo FP90 central processor and FP8902H hot stage attachment. Little to no change in the visual appearance of the powder was observed with the dry preparations. The neat (NM1392-04) and the zinc (NM1392-05) formulations demonstrated some particles "popping" or jumping of particles at approximately 80° C. For all formulations evaluated in high temperature immersion oil, channels formed at approximately 90° C., and at 110° C. outgassing was observed. It is assumed that this outgassing is due to water loss from the powder. The elongated time for this outgassing is consistent with the downward sloping profiles observed by DSC.

Example 5

Chemical Characterization of IL-4R Powder Formulations

Several techniques can be used to analyze the samples of Example 1 to determine the extent of aggregation and degradation. Insoluble aggregates were determined by visible detection and UV spectrophotometry. Soluble aggregates were analyzed quantitatively by size exclusion chromatography and qualitatively by SDS-PAGE.

Example 5(A): Size Exclusion High pressure Liquid Chromatography (SE-HPLC)

Soluble aggregates were measured quantitatively by SE-HPLC. Samples were stored at 5° C. until injection. Chomatograms were extracted and processed at 220 nm.

The percentage monomer content of the formulated solutions before spray drying was compared to the corresponding reconstituted aerosol drug powders. There were no significant changes in the percentage monomer content between the formulated solutions and the reconstituted aerosol drug powders. Results are set forth in Table 6 below.

Based on results obtained from the powder stability temperature data at two weeks, as the storage temperature increased, the amount of monomer content compared to the initial time data decreased. The largest change in percentage monomer from initial was at 50° C. with a range of 2.1%, in the neat formulation, to 1.9% in both the zinc and citrate formulations. In the 2 week powder stability humidity study, the citrate formulations exhibited the largest drop of just 1.8% in monomer from initial at the extreme RH of 75%. This was probably due to citrate crystallization. Thus, the IL-4R compositions of the invention exhibit essentially no thermal degradation upon spray-drying (as evidenced by monomer content of the illustrative compositions), and exhibit a minimal decrease in monomer upon storage, under a variety of illustrative temperature and humidity conditions. Unlike other proteins, which upon spray drying are often prone to significant aggregation (Maa, Y. F., et al., *J. of Pharmaceutical Sciences*, Vol 87 (2), p. 152-159 (1997)), IL-4R has been found to be surprisingly resistant and impervious to such conditions, and forms spray-dried powders in which the protein exhibits insignificant degradation even in the absence of commonly-employed stabilizing/protecting excipients.

Two 1 mg/mL liquid samples stored at 25 and 50° C. for 2 weeks were evaluated as controls. The liquid sample stored at 25° C. had a 0.7% dimer content expressed as a percentage of monomer, but had over 17% of low molecular weight species. At 50° C., the liquid had 2.3% dimer content expressed as a percentage of monomer and 2.1% of low molecular weight species. Samples were prepared and retested and the original results were confirmed. The percentage drop in monomer content of the IL-4R liquid formulation at 50° C. for 2 weeks is approximately 40% from initial (See Table 6 and FIGS. 1, 2, and 3), while powdered formulations remained essentially unchanged. Thus, solution formulations of IL-4R are significantly more unstable (i.e., prone to degradation) than the corresponding powder formulations stored under essentially the same conditions for a given period of time. Interestingly, the extreme conditions of temperature and shear experienced by the IL-4R molecule in solution during spray-drying did not cause a significant drop in monomer content or promote extensive chemical degradation of the molecule such as that observed for the liquid samples placed on storage. The above data points to the striking advantage of powder formulations of IL-4R over corresponding liquid formulations upon storage, based upon both chemical and physical stability data.

Example 5(B): Ultraviolet Spectroscopy (UV)

UV spectrophotometric analyses were used to evaluate turbidity (i.e., aggregation/precipitation) in reconstituted samples. Measurements were performed on a Hitachi U-3000, dual beam spectrophotometer. Instrument parameters were set at a scan rate of 300 nm/min; 1.0 nm slit width; and a scan ranged from 450 nm to 200 nm. Samples were visually inspected for particulate matter. Insoluble aggregates were determined quantitatively by measuring the turbidity of the solution with UV. Linear regression to correct for scatter was performed from absorbance values at 350, 375 and 400 nm. Absorbance at $\lambda_{max}$ corrected for light scattering was extrapolated from the equation for the regression line. The percent insoluble aggregate is the percentage of absorbance corrected for light scattering, divided by absorbance uncorrected at λmax as shown in Eq. 1 below.

$$\% \text{ percent insoluble aggregates} = \frac{\text{Abs}\lambda_{max}(\text{light scatter corrected})}{\text{Abs}\lambda_{max}(\text{light scatter uncorrected})} \quad (\text{Eq. 1})$$

Samples were either reconstituted or diluted to a concentration of 0.1 mg of IL-4R peptide/mL with water prior to analysis.

Except for one sample, all solution samples, before and after spray drying, had no visible signs of particulate matter or had less than 5% calculated insoluble aggregates. The spray dried neat formulation, Formulation 1(A), was visibly clear under initial conditions but had 7% insoluble aggregates, when calculated by Eq 1. Since the 2 week stability time point for this sample contained only 3% insoluble aggregates, it was concluded that the initial value was in error. All samples after exposure for 2 weeks to specified temperature and humidity conditions exhibited no visible signs of particulates or detectable insoluble aggregates. Less than 3.5% insoluble aggregates were calculated using Eq. 1 for all batches. Table 6 includes data collected only by SE-HPLC and does not contain insoluble aggregate information.

TABLE 6

Aggregation Summary for IL-4R Formulations (SE-HPLC)

| | Monomer Content (%) | | | | | | | |
|---|---|---|---|---|---|---|---|---|
| | Neat | | Zn:IL-4R | | Citrate | | Leucine | |
| | Initial | 2 weeks | Initial | 2 weeks | Initial | 2 weeks | Initial | 2 weeks |
| Pre-SD Solution | 96.4 | | 96.0 | | 95.0 | | 96.1 | |
| 2-8° C. | 96.5 | 96.0 | 96.2 | 95.9 | 95.1 | 94.7 | 96.0 | 95.9 |
| 25° C. | 96.5 | 96.0 | 96.2 | 95.6 | 95.1 | 94.6 | 96.0 | 95.6 |
| 40° C. | 96.5 | 95.4 | 96.2 | 95.0 | 95.1 | 94.3 | 96.0 | 95.3 |
| 50° C. | 96.5 | 94.4 | 96.2 | 94.3 | 95.1 | 93.2 | 96.0 | 94.6 |
| 25° C./0% RH | 96.5 | 96.0 | 96.2 | 95.6 | 95.1 | 94.6 | 96.0 | 95.6 |
| 25° C./33% RH | 96.5 | 95.7 | 96.2 | 95.4 | 95.1 | 94.5 | 96.0 | 95.3 |
| 25° C./75% RH | 96.5 | 95.4 | 96.2 | 95.3 | 95.1 | 93.5 | 96.0 | 94.9 |

Example 5(C): Sodium Dodecyl Sulfate-PolyacrEylamide Gel Electrophoresis (SDS-PAGE)

Soluble aggregates and degradation were measured qualitatively by SDS PAGE using a Novex Silver Xpresss staining kit. Novex pre-cast 4-20% tris-glycine gels were run on a Novex Xcell II electophoresis mini-cell. Samples were either reconstituted or diluted to a concentration of 0.1 mg of IL-4R peptide/mL with water. Solutions were prepared under reducing and non-reducing conditions and applied at a load of 1-5 μg of protein per lane. The 5 μg protein loads were run to try and enhance detection of bands not observable in the 1 μg protein load. Reduced samples were treated with 2-mercaptoethanol and heated at 100° C. for 3 minutes. Gels were run at 125V, 25 mA/gel until the gel front reached the bottom (approx 1.5 hrs). In addition to the pre-spray dry solution, initial powders, and stability samples, a solution of 1 mg IL-4R peptide/mL was analyzed as a control Reducing and non-reducing gels were run for the liquid formulation at initials, 2 weeks, 25° C. and 2 weeks, 40° C.

There were no changes in the gel profiles between the formulated solutions before spray drying and the reconstituted aerosol drug powders. The monomer bands of all samples and controls of IL-4R on the gels ran at higher molecular weight (approx. 50 kDa) than reported values and appear broad and diffuse. This is most likely attributed to the protein being a glycoslyated and affecting the migration of IL-4R through the gel. There was another distinct band running at approximately 97 kDa, this was attributed to the dimer which is presumably the dimer form of the protein. Several lower molecular weight banks were visible in the 5 μg load gel that have not been identified.

As with the initials, there were no visible changes in the stability gel profiles of the 2 weeks bulk aerosol powder in either the temperature of the humidity studies compared to the control solution. The neat IL-4R sample incubated at 25° C., 75% RH for two 2 weeks was not detected in the original gel, probably due to dilution error. Upon repeat analysis, the sample was equivalent to the other stability samples. Gels of the IL-4R solution samples showed a great degree of degradation and aggregation compare to the spray dried powders.

In sum, based on the results obtained from the stability study, IL-4R was observed to be chemically stable in all four lots of bulk powder formulations (Formulations 1(A)-1(D)) for up to two weeks at 2-8° C., 25° C., 40° C. and 50° C., in addition to 25° C. at 0%, 33% and 75% RH for powders stored naked. No insoluble aggregation was observed by UV for all the batches. Monomer content dropped by less than 2% for all formulations at these conditions, with the citrate formulation exhibiting the greatest reduction in monomer content upon storage.

The disclosure of each publication, patent or patent application mentioned in this specification is incorporated by reference herein to the same extent as if each individual publication, patent or patent application were specifically and individually indicated to be incorporated by reference.

Although the foregoing invention has been described in some detail by way of illustration and example, for purposes of clarity of understanding, it will be apparent to those skilled in the art that certain changes and modifications may be practiced within the scope of the appended claims.

What is claimed:

1. A method for preparing a dry powder composition of soluble Interleukin-4 receptor (IL-4R), said method comprising:
    (a) preparing a mixture or a solution of soluble IL-4R and one or more excipients selected from the group consisting of carbohydrates, lipids, divalent metal cations, buffers, amino acids, oligopeptides, peptides, and proteins, in solvent, and
    (b) spray-drying the mixture or solution to obtain a spray-dried powder comprising IL-4R; wherein the powder composition comprises particles having a mass median aerodynamic diameter (MMAD) of less than about 10 microns.

2. The method of claim 1, wherein the excipient is a carbohydrate.

3. The method of claim 2, wherein the carbohydrate is a sugar or sugar alcohol.

4. The method of claim 1, wherein the excipient is an amino acid.

5. The method of claim 4, wherein the amino acid is a hydrophobic amino acid.

6. The method of claim 1, wherein the excipient is selected from the group consisting of citrate salts, leucine, raffinose, zinc salts, and combinations thereof.

7. The method of claim 1, wherein the excipient is a buffer.

8. The method of claim 1, wherein the excipient is a divalent metal cation.

9. The method of claim 1, wherein the spray-dried powder comprises particles having a mass median aerodynamic diameter (MMAD) of less than about 5 microns.

10. The method of claim 1, wherein the spray-dried powder comprises particles having a mass median aerodynamic diameter (MMAD) of less than about 3.5 microns.

11. The method of claim 1, wherein the spray-dried powder comprises particles having a mass median diameter (MMAD) of between about 0.1 to 3 microns.

12. The method of claim 1, wherein the spray-dried powder has a residual moisture content of less than about 10% by weight.

13. The method of claim 1, wherein the spray-dried powder has a residual moisture content of less than about 5% by weight.

14. The method of claim 1, wherein the spray-dried powder has a bulk density ranging from about 0.1-10 g/cc.

15. The method of claim 1, wherein the mixture or solution of IL-4R contains IL-4R dissolved in a concentration from 0.01% (weight/volume) to 20% (weight/volume).

16. The method of claim 1, wherein the solvent comprises a water-miscible solvent.

17. The method of claim 16, wherein the water-miscible solvent is selected from the group consisting of acetone and alcohols.

* * * * *